United States Patent
Hebrank

(10) Patent No.: US 6,860,225 B2
(45) Date of Patent: Mar. 1, 2005

(54) METHODS AND APPARATUS FOR IDENTIFYING LIVE EGGS BY DETECTING EMBRYO HEART RATE AND/OR MOTION

(75) Inventor: John H. Hebrank, Durham, NC (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 10/427,569

(22) Filed: May 1, 2003

(65) Prior Publication Data

US 2004/0107912 A1 Jun. 10, 2004

Related U.S. Application Data

(60) Provisional application No. 60/380,049, filed on May 6, 2002.

(51) Int. Cl.[7] ............................................. A01K 45/00
(52) U.S. Cl. ........................................................ 119/6.8
(58) Field of Search ...................... 119/6.8, 348, 328; 436/21; 356/51, 52, 53, 54, 55, 64, 66

(56) References Cited

U.S. PATENT DOCUMENTS

| | | | |
|---|---|---|---|
| 2,477,752 A | 8/1949 | Kiss .................................. 119/1 |
| 2,636,925 A | 4/1953 | Gascoigne ..................... 175/183 |
| 2,762,365 A | 9/1956 | Wagner et al. .................. 128/1 |
| 2,851,006 A | 9/1958 | Taylor et al. ..................... 119/1 |
| 3,037,479 A | 6/1962 | Flory ............................... 119/1 |
| 3,077,993 A | 2/1963 | Mulvany et al. ................ 214/1 |
| 3,120,834 A | 2/1964 | Goldhaft et al. ................ 119/1 |
| 3,123,045 A | 3/1964 | Cosgrove et al. ............... 119/1 |
| 3,139,300 A | 6/1964 | Hirt ................................. 294/65 |
| 3,256,856 A | 6/1966 | Nicely et al. ................... 119/1 |
| 3,377,989 A | 4/1968 | Sandhage et al. ............... 119/1 |
| 3,420,743 A | 1/1969 | Sandhage et al. ........... 195/104 |
| 3,506,140 A | 4/1970 | Koch et al. ..................... 214/1 |
| 3,540,824 A | 11/1970 | Fonda et al. .................. 356/53 |
| 3,594,285 A | 7/1971 | Noren ........................ 195/127 |
| 3,606,960 A | 9/1971 | Butterworth ................. 221/211 |
| 3,616,262 A | 10/1971 | Coady et al. ................ 195/127 |
| 4,019,430 A | 4/1977 | Warren .......................... 99/485 |
| 4,039,259 A | 8/1977 | Saito et al. .................... 356/53 |
| 4,040,388 A | 8/1977 | Miller ............................ 119/1 |
| 4,045,073 A | 8/1977 | Mosterd ......................... 294/87 |
| 4,355,936 A | 10/1982 | Thomas et al. ............. 414/118 |
| 4,458,630 A | 7/1984 | Sharma et al. ................. 119/1 |
| 4,469,047 A | 9/1984 | Miller ............................ 119/1 |
| 4,593,646 A | 6/1986 | Miller et al. ................... 119/1 |
| 4,604,038 A | 8/1986 | Belew ........................ 417/475 |
| 4,671,652 A | 6/1987 | van Asselt et al. ........... 356/66 |
| 4,681,063 A | 7/1987 | Hebrank ........................ 119/1 |
| 4,822,605 A | 4/1989 | Powell ....................... 424/85.2 |
| 4,903,635 A | 2/1990 | Hebrank ........................ 119/1 |
| 4,928,628 A | 5/1990 | Gassman et al. .............. 119/1 |
| 4,928,629 A | 5/1990 | Trampel ........................ 119/1 |
| 5,056,464 A | 10/1991 | Lewis .......................... 119/6.8 |
| 5,136,979 A | 8/1992 | Paul et al. ................... 119/6.8 |

(List continued on next page.)

FOREIGN PATENT DOCUMENTS

| | | |
|---|---|---|
| FR | 2 755 580 | 5/1998 |
| SU | 1226308 | 3/1983 |
| WO | WO 02/086495 | 10/2002 |
| WO | 2004023136 | 3/2004 |

Primary Examiner—Yvonne R. Abbott
(74) Attorney, Agent, or Firm—Myers Bigel Sibley & Sajovec, P.A.

(57) ABSTRACT

Methods and apparatus for identifying live eggs utilize a cup having a photodetector therewithin that overlies a portion of an egg. The egg is illuminated via a light source positioned adjacent the egg. Variations in the intensity of light passing through the egg is detected via the photodetector which generates an output signal corresponding to detected light intensity. The output signal is processed to identify cyclical and non-cyclical variations in light intensity. The egg is designated as a live egg in response to identifying cyclical and/or non-cyclical variations in light intensity.

58 Claims, 9 Drawing Sheets

U.S. PATENT DOCUMENTS

| | | |
|---|---|---|
| 5,173,737 A | 12/1992 | Mitchell et al. ............... 356/53 |
| 5,176,101 A | 1/1993 | Paul et al. ................... 119/6.8 |
| 5,182,571 A | 1/1993 | Creagh et al. ............... 346/1.1 |
| 5,504,572 A | 4/1996 | Taylor et al. ................. 356/53 |
| 5,745,228 A | 4/1998 | Hebrank et al. .............. 356/53 |
| RE35,973 E | 12/1998 | Paul et al. ................... 119/6.8 |
| 5,900,929 A | 5/1999 | Hebrank et al. .............. 356/52 |
| 5,983,830 A * | 11/1999 | Cox et al. .................... 119/6.8 |
| 6,032,612 A | 3/2000 | Williams ..................... 119/6.8 |
| 6,373,560 B1 | 4/2002 | Roux .......................... 356/58 |
| 6,488,156 B1 | 12/2002 | Cohen ....................... 209/510 |
| 6,504,603 B1 | 1/2003 | Schouenborg ............... 356/53 |
| 6,535,277 B2 | 3/2003 | Chalker, II et al. ........... 356/53 |
| 2002/0157613 A1 | 10/2002 | Phelps et al. .............. 1199/6.8 |

* cited by examiner

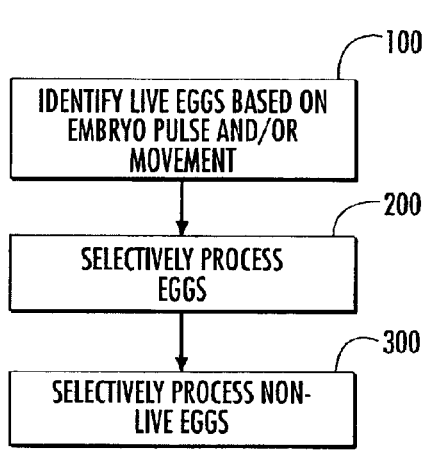
FIG. 2.
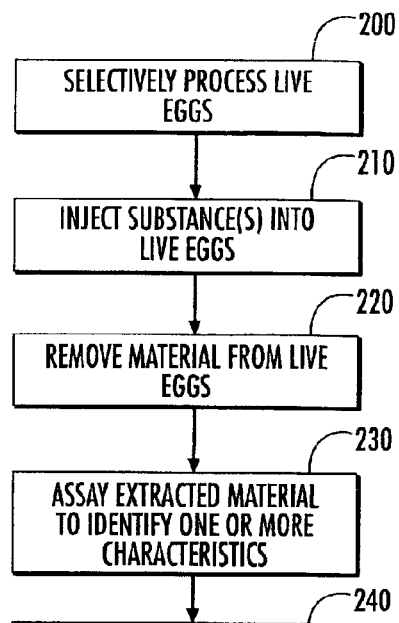
FIG. 4.
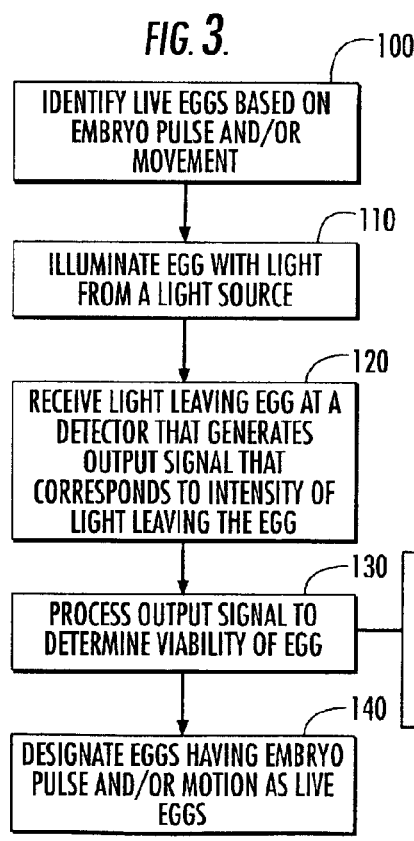
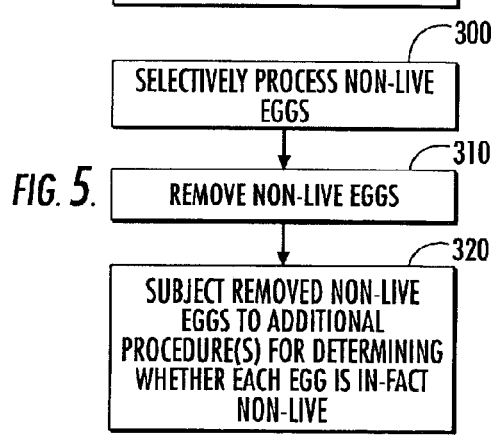
FIG. 5.
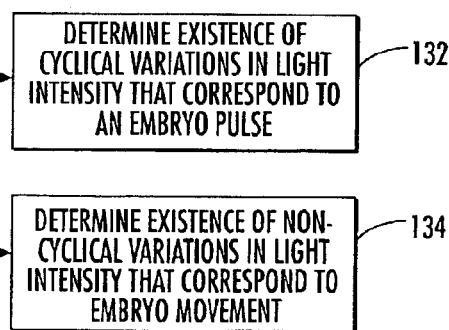

METHODS AND APPARATUS FOR IDENTIFYING LIVE EGGS BY DETECTING EMBRYO HEART RATE AND/OR MOTION

RELATED APPLICATION

This application claims the benefit of U.S. Provisional Application No. 60/380,049, filed May 6, 2002, the disclosure of which is incorporated herein by reference in its entirety as if set forth fully herein.

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to herein as "non-live eggs"). Non-live eggs are removed from incubation to increase available incubator space. In many instances it is desirable to introduce a substance, via in ovo injection, into a live egg prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. An example of an injection device is disclosed in U.S. Pat. No. 4,681,063 to Hebrank; this device positions an egg and an injection needle in a fixed relationship to each other, and is designed for the high-speed automated injection of a plurality of eggs. The selection of both the site and time of injection treatment can also impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for identifying live eggs and selectively injecting only live eggs, is desirable.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-live. Non-live eggs are manually removed before the eggs are conveyed to the inoculating station.

An egg may be a "live" egg, meaning that it has a viable embryo. FIG. 1A illustrates a live poultry egg 1 at about day one of incubation. FIG. 1B illustrates the live egg 1 at about day eleven of incubation. The egg 1 has a somewhat narrow end in the vicinity represented at 1a as well as an oppositely disposed broadened end portion in the vicinity shown at 1b. In FIG. 1A, an embryo 2 is represented atop the yolk 3. The egg 1 contains an air cell 4 adjacent the broadened end 1b. As illustrated in FIG. 1B, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead", "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

There are other applications where it is important to be able to distinguish between live and non-live eggs. One of these applications is the cultivation and harvesting of vaccines via live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the agnostic fluid from the egg. Typically, eggs are candled before injection of a seed virus to remove non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 4,671,652 to van Asselt et al. describes a candling apparatus in which a plurality of light sources and corresponding light detectors are mounted in an array, and wherein eggs are passed on a flat between the light sources and the light detectors.

Unfortunately, conventional candling techniques may have somewhat limited accuracy, especially at high candling through-put speeds. Pulsed light opacity identification systems can operate at speeds equivalent to about 300,000 eggs per hour and successfully identify clear eggs from a stream of eggs. However, some eggs identified as being live will in fact be non-live (e.g., rotted eggs, mid and late dead eggs).

Thermal-based candling systems can detect rotted eggs in egg streams of up to 50,000 eggs per hour. Unfortunately, because of egg-to-egg thermal variations, thermal-based candling systems may misidentify live and non-live eggs. In addition, thermal-based candling systems may not be accurate with embryos that generate less heat than day 17 eggs.

Embryo heartbeat (pulse) detection methods are known that can detect live eggs with a high degree of accuracy. For example, Buddy by Avitronics (Truro, England) can detect avian embryo heartbeats. Detection happens in about five to ten seconds for about 60% of eggs, with near 100% detection requiring 60 second sampling times. Unfortunately, the time required to detect a live egg is prohibitively slow for use in hatcheries where high through-put rates are required. For automated pulse detection to be a useful method of determining viable eggs, a much shorter processing time is needed to read hatchery volumes of eggs (typically several hundred thousand in six to eight hours).

U.S. Pat. No. 5,173,737 to Mitchell describes a method of determining whether an egg contains a live embryo by directing light into an egg to stimulate embryo movement, and then measuring resulting embryo movement. Unfortunately, the Mitchell method may be time-consuming and may not accurately detect live embryos that do not move as a result of light stimulation.

SUMMARY OF THE INVENTION

In view of the above discussion, a method of identifying live eggs is provided that includes: contacting an egg with a cup; illuminating the egg with light from one or more selected portions of the spectrum via a light source positioned adjacent the egg; detecting the intensity of light leaving the egg via a photodetector positioned within the cup; generating an output signal that corresponds to detected light intensity; processing the output signal to identify cyclical and non-cyclical variations in light intensity; and designating the egg as a live egg in response to identifying cyclical and/or non-cyclical variations in light intensity. Cyclical variations in light intensity may indicate the existence of an embryo pulse and non-cyclical variations in light intensity indicate embryo movement.

According to other embodiments of the present invention, a method of processing eggs includes: illuminating each of a plurality of eggs with light from a light source; detecting light leaving each egg via a respective photodetector positioned adjacent each egg, wherein each photodetector generates a respective output signal that corresponds to intensity of light leaving a respective egg; processing the output signal to identify cyclical and non-cyclical variations in light intensity; designating an egg as a live egg in response to identifying cyclical and/or non-cyclical variations in light intensity; and selectively processing eggs designated as live eggs.

According to embodiments of the present invention, selectively processing eggs designated as live eggs may include: extracting material (e.g., allantoic fluid, amnion, yolk, shell, albumen, tissue, membrane, blood, etc.) from each egg designated as being live; assaying the material extracted from each egg to identify live eggs having one or more characteristics (e.g., gender, etc.); and selectively processing (e.g., injecting a vaccine, virus, etc. into) live eggs identified as having the one or more characteristics.

According to other embodiments of the present invention, an apparatus for identifying live eggs includes a generally horizontal frame movable between raised and lowered positions, and a plurality of detector tools supported by the frame in generally vertical orientations and movable with the frame between the raised and lowered positions. Each detector tool includes a light source that is configured to be positioned adjacent an egg when the frame is in the lowered position and to illuminate the egg with light from one or more selected portions of the spectrum. Each detector tool includes a cup that is configured to overlie an egg in contacting relationship therewith when the frame is in the lowered position. A photodetector is disposed within the cup and generates an output signal corresponding to intensity of light leaving the egg. A processor communicates with each photodetector and processes the output signals from each photodetector to identify cyclical and/or non-cyclical variations in light intensity.

According to other embodiments of the present invention, an apparatus for identifying live eggs includes an egg support that is movable between retracted and extended positions, a frame that overlies the egg support, and a plurality of detector tools supported by the frame. Because egg heights can vary (often by 0.75 inch or more), the egg supports individually lift respective eggs so that the tops of all the eggs are at the same height. Each detector tool includes a cup that is configured to overlie an egg in contacting relationship therewith when the egg support is in the extended position. A photodetector is disposed within the cup and generates an output signal corresponding to intensity of light from a light source passing through the egg. A processor communicates with each photodetector and processes the output signals from each photodetector to identify cyclical and/or non-cyclical variations in light intensity.

Embodiments of the present invention are advantageous because embryo pulse and movement detection occurs from above the eggs in a flat, thereby eliminating complications that can be caused by foreign material, such as dust, debris and water in the flat. Moreover, embodiments of the present invention can facilitate embryo pulse and movement detection with eggs of varying size and with eggs having non-vertical orientations.

BRIEF DESCRIPTION OF THE DRAWINGS

FIGS. 2–5 are flowcharts of operations for identifying live and non-live eggs and for selectively processing same, according to embodiments of the present invention.

DETAILED DESCRIPTION OF THE INVENTION

Figure 1B:
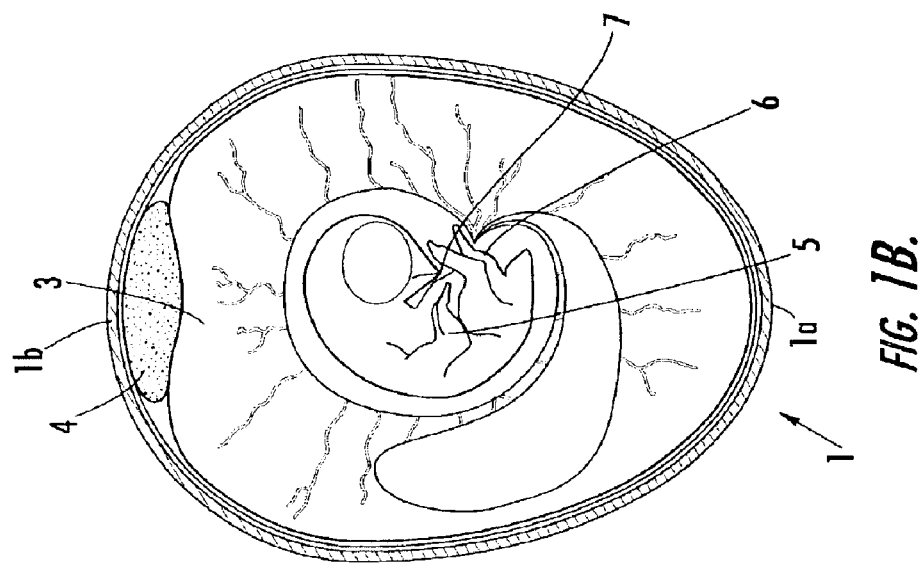
FIG. 1B illustrates a live chicken egg at about day eleven of incubation.
Figure 1A:
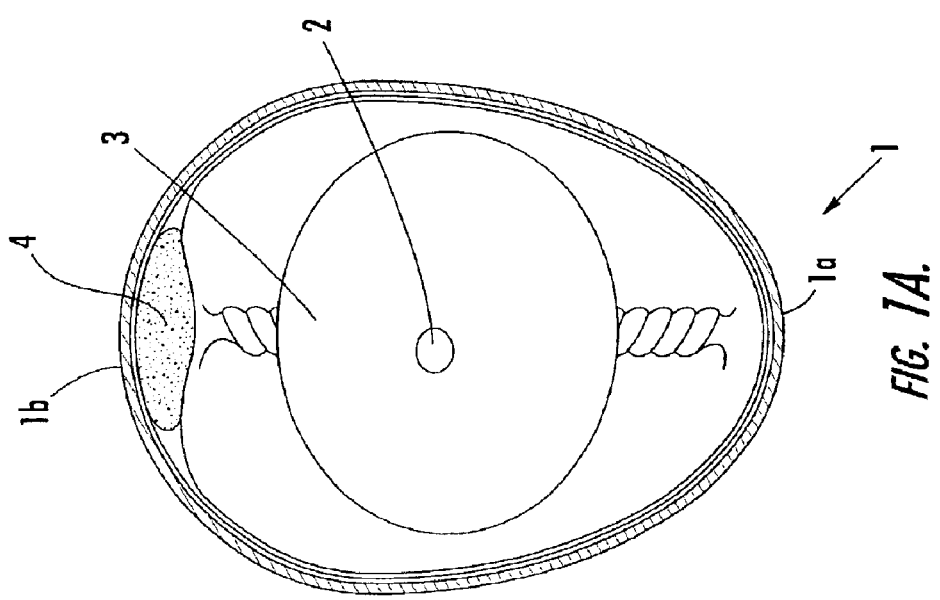
FIG. 1A illustrates a live chicken egg at about day one of incubation.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise.

All publications, patent applications, patents, and other references mentioned herein are incorporated by reference in their entirety.

In the drawings, the thickness of lines, layers and regions may be exaggerated for clarity. It will be understood that when an element such as a layer, region, substrate, or panel is referred to as being "on" another element, it can be directly on the other element or intervening elements may also be present. In contrast, when an element is referred to as being "directly on" another element, there are no intervening elements present. It will be understood that when an element is referred to as being "connected" or "attached" to another element, it can be directly connected or attached to the other element or intervening elements may also be present. In contrast, when an element is referred to as being "directly connected" or "directly attached" to another element, there are no intervening elements present. The terms "upwardly", "downwardly", "vertical", "horizontal" and the like are used herein for the purpose of explanation only.

Methods and apparatus according to embodiments of the present invention may be utilized for accurately identifying live and non-live eggs at any time during embryonic development (also referred to as the incubation period). Embodiments of the present invention are not limited to identification only at a particular day (e.g., day eleven) or time period during the embryonic development period. In addition, methods and apparatus according to embodiments of the present invention may be used with any types of avian eggs including, but not limited to, chicken, turkey, duck, geese, quail, pheasant eggs, exotic bird eggs, etc.

Referring now to FIG. 2, methods of processing eggs in accordance with embodiments of the present invention are illustrated. Live eggs are identified based on the identification of an embryo pulse and/or embryo movement (Block 100). Eggs identified as live may be selectively processed (Block 200) and eggs identified as non-live may be selectively processed (Block 300).

Referring to FIG. 3, identification of live eggs based upon embryo pulse and/or movement (Block 100) can be performed rapidly and with high accuracy. Each egg in a plurality of presumably embryonated eggs is illuminated with light from a light source (Block 110). The light may include light in either or both visible and infrared wavelengths. Light leaving each egg is then received by a photodetector positioned adjacent each egg (Block 120). Each photodetector generates an output signal that corresponds to the intensity of light leaving a respective egg. The output signal is processed to determine the viability of each egg (Block 130). Eggs having an embryo pulse and/or movement are designated as live eggs (Block 140).

Viability may be determined by processing the output signal to determined the existence of cyclical variations in light intensity that correspond to an embryo pulse (Block 132). Viability may be determined by processing the output signal to determine the existence of non-cyclical variations in light intensity that correspond to embryo movement (Block 134). In addition, viability may be determined by processing the output signal to determine the existence of both cyclical and non-cyclical variations in light intensity.

Referring to FIG. 4, selectively processing live eggs (Block 200) may include injecting one or more substances (e.g., vaccines, antibiotics, vitamins, etc.) into live eggs (Block 210). Selective processing may also include removing material from live eggs (Block 220).

Removal of material may be in addition to injecting one or more substances. Removing material from an egg may include extracting allantoic fluid, amnion, yolk, shell, albumen, tissue, membrane and/or blood from each egg. In addition, removing material from live eggs may include harvesting virus from the eggs.

Removed material may be assayed to identify one or more characteristics (e.g., gender, pathogen content, genetic markers related to bird health or performance, nutritional, endocrine or immune indicators or factors, etc.) of the respective egg (Block 230). The live eggs identified as having the one or more characteristics are then selectively processed (Block 240). Selective processing may include injecting substances into the eggs, removing material, etc. For example, one or more substances may be injected into live eggs according to gender. Selective processing may include removing eggs identified as having the same characteristic (e.g., gender).

Eggs not designated as live eggs may be selectively processed (Block 300, FIG. 2). Referring to FIG. 5, selective processing of non-live eggs may include removing non-live eggs (Block 310). Removed eggs may be discarded or used for other purposes. In addition, removed eggs may be subjected to one or more additional procedures for determining whether or not each egg is in-fact non-live (Block 320). For example, each egg initially determined to be non-live may be subjected to human light candling, thermal candling, etc., or some other known procedure to confirm that that the egg is accurately identified as non-live.

Figure 6A:
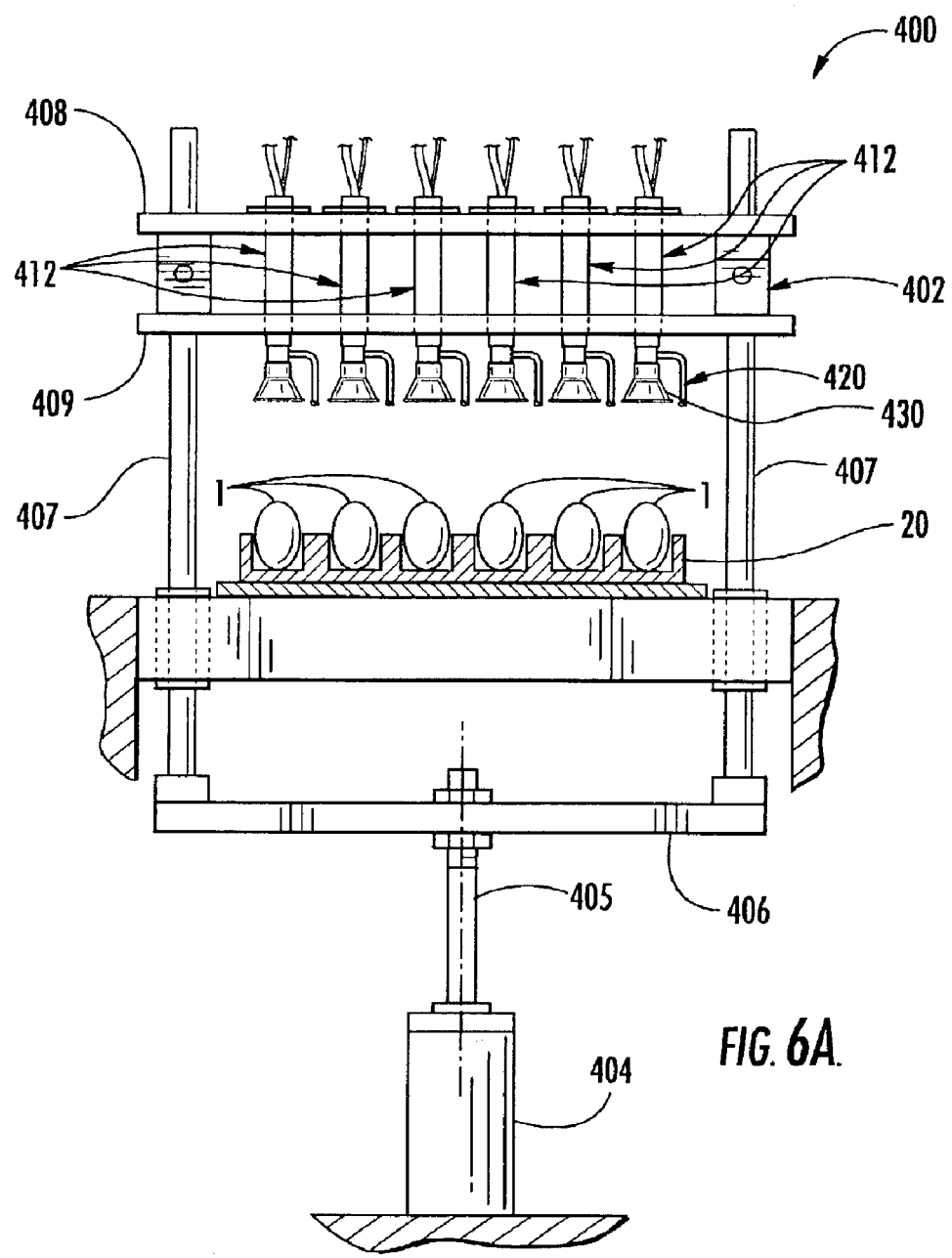
FIG. 6A is a side elevation view of an apparatus for identifying live eggs according to embodiments of the present invention, wherein the frame is in the retracted position.
Figure 6B:
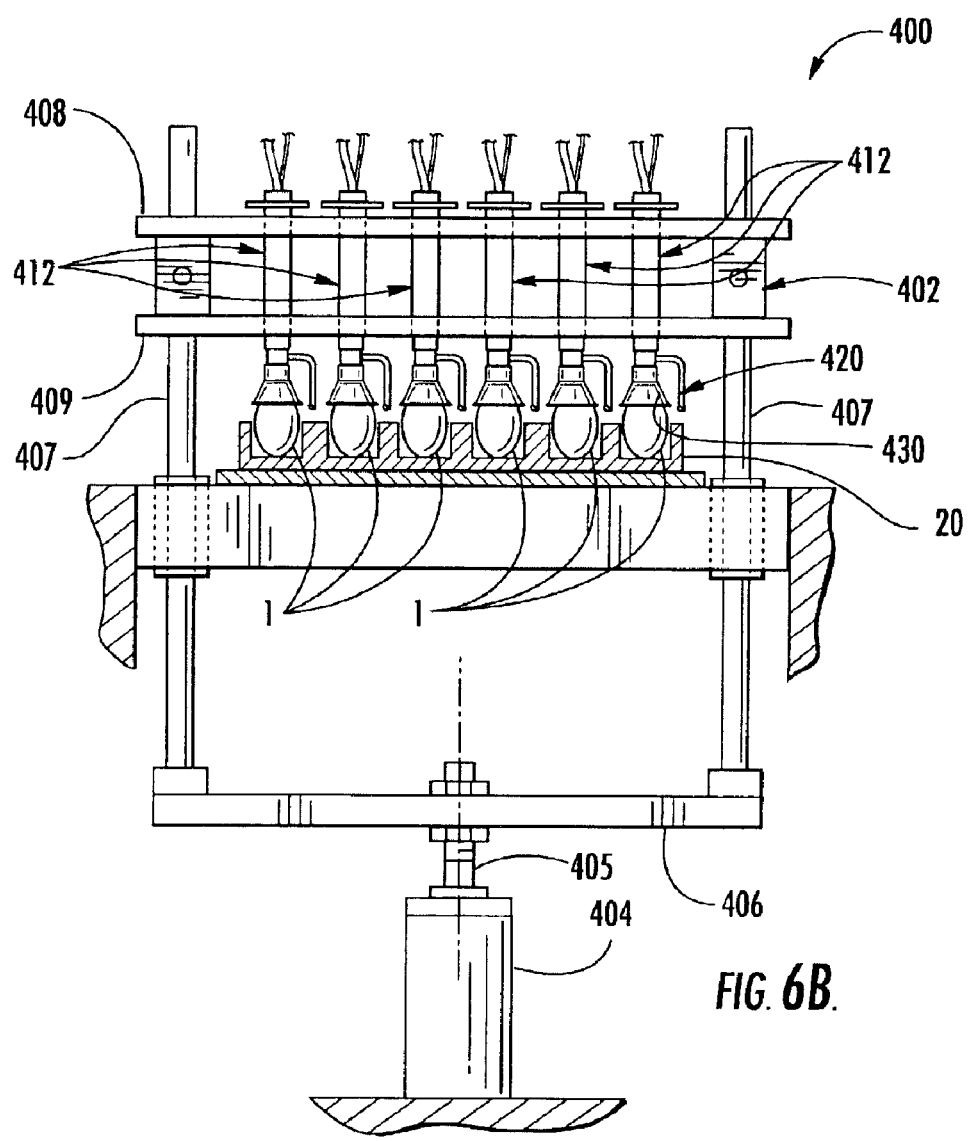
FIG. 6B illustrates the apparatus of FIG. 6A with the frame in the extended position.
Figure 6C:
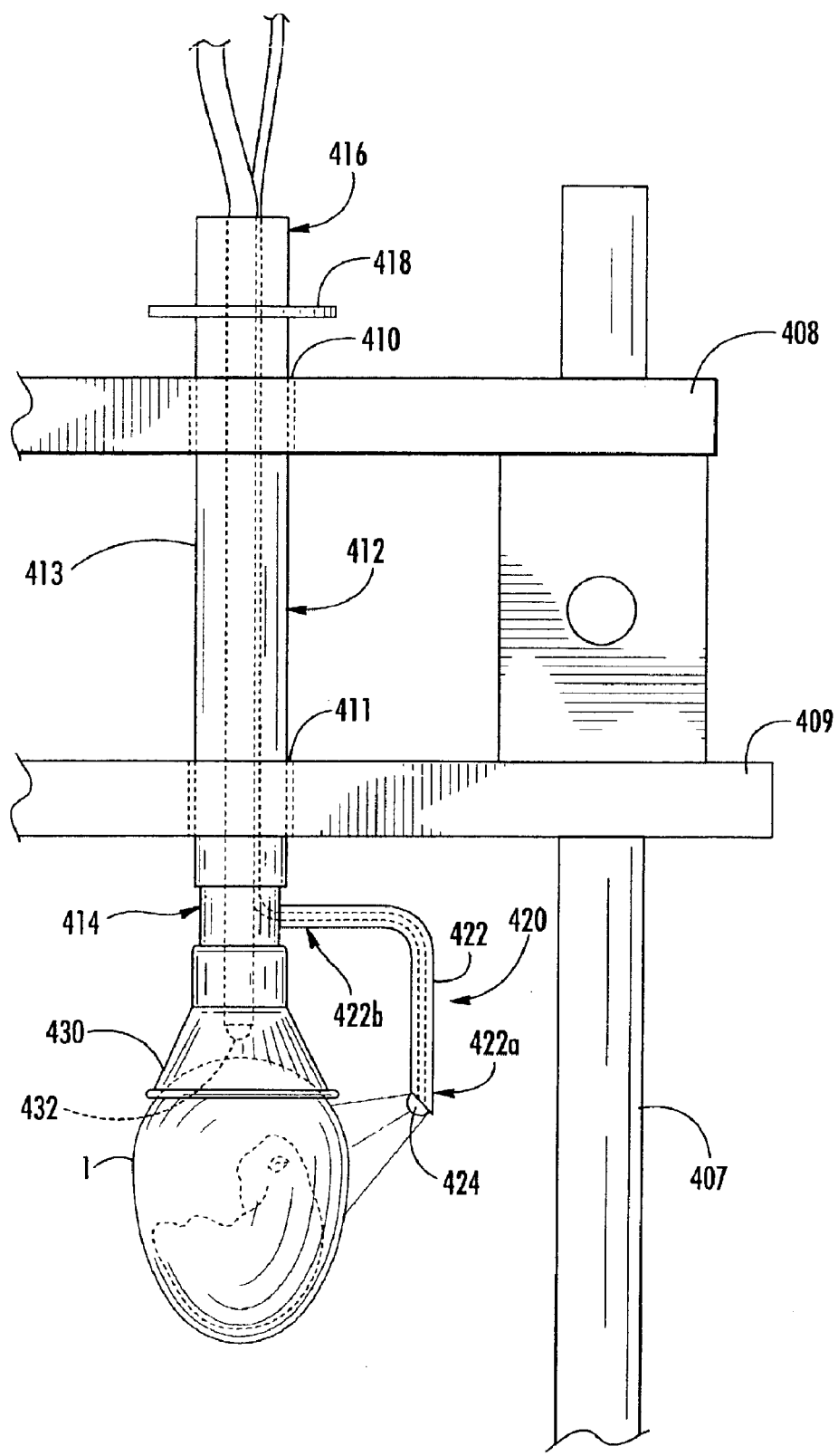
FIG. 6C is an enlarged view of one of the detector tools of FIGS. 6A–6B.

Referring to FIGS. 6A–6C, an apparatus 400 for identifying live eggs according to embodiments of the present invention is illustrated. The apparatus 400 includes a frame 402 that is movable between a raised position (FIG. 6A) and a lowered position (FIG. 6B). The invention includes means, shown as the cylinder 404, cylinder shaft 405, horizontal member 406 and upright shafts 407, for raising and lowering the frame 402 and the detector tools suspended therefrom. However, embodiments of the present invention are not limited to the illustrated means for raising and lowering the frame 402. Various arrangements for raising and lowering frame 402 can be used in accordance with embodiments of the present invention. Moreover, embodiments of the present invention are not limited to the illustrated configuration of frame 402.

The illustrated frame 402 includes upper and lower plates 408, 409 in spaced-apart relationship. Each plate includes a respective array of openings 410, 411 formed therethrough. A plurality of detector tools 412 are supported in a generally vertical orientation via the upper plate 408. Each detector tool 412 has an elongated member 413 that extends through respective openings 410, 411 in the upper and lower plates 408, 409. A lower portion (broadly designated as 414) of each detector tool 412 depends downwardly below the lower plate 409. An upper portion (broadly designated as 416) of each detector tool 412 extends above the upper plate 408. A clip 418 is secured to the upper portion 416 of each detector tool 412. When the frame 402 is in the raised position (FIG. 6A), the upper plate 408 supports the detector tools 412 via respective clips 418. When the frame 402 is moved to the lowered position (FIG. 6B–6C) each detector tool 412 rests on top of a respective egg 1 and clips 418 are not supported by upper plate 408. The openings 410, 411 in the upper and lower plates 408, 409 permit translational movement of the detector tools 412 to accommodate different egg sizes, shapes and orientations.

A light source 420 depends from each detector tool lower portion 414, as illustrated. Each light source 420 is configured to be positioned adjacent a portion of an egg 1 when the frame 402 is in the lowered position (FIG. 6B–6C). The light source 420 is configured to illuminate the egg 1 with light from one or more selected portions of the spectrum. For example, the light source 420 may be configured to illuminate the egg 1 with light in the visible portion of the spectrum and/or light from the infrared portion of the spectrum.

In the illustrated embodiment, the light source 420 includes an elongated stalk 422 having a free end 422a. An opposite end 422b is secured to the detector tool 412. A light-emitting element (e.g., one or more light emitting diodes (LEDs)) 424 is positioned at the stalk free end 422a. According to embodiments of the present invention, a plurality of light-emitting elements may be positioned at the stalk free end 422a. Embodiments of the present invention are not limited to the use of LEDs. Optical fibers and light pipes may be utilized to provide light from a source.

Embodiments of the present invention are not limited to the illustrated light source 420 or to the light source 420 being secured to the detector tool 412. The light source 420 may be secured to various portions of the frame 402 as well as to other devices.

A cup 430 is attached to the detector tool lower portion 414, as illustrated, and is configured to overlie a portion of an egg 1 in contacting relationship therewith when the frame 402 is in the lowered position. The weight of the detector tool 412 is sufficient to seat the cup 430 on an egg such that stray light cannot enter the cup 430. Alternatively, or additionally, vacuum may be provided within the cup to facilitate seating the cup 430 on an egg 1.

A photodetector 432 is disposed within the cup 430 and is configured to generate an output signal corresponding to the intensity of light leaving an egg 1. According to embodiments of the present invention, the photodetector is provided with an integral amplifier to limit environmental electrical noise (e.g., 60 Hz from power lines). According to embodiments of the present invention, a filter may be utilized to block wavelengths other than wavelengths emitted by the light source 420. For example, if the light source 420 illuminating an egg emits 880 nM infrared light, then a reduction in sensitivity to external light (like mercury vapor lighting and fluorescent lighting) can be achieved with a photodetector module having a filter that blocks visible light. Amplifiers and filters are well known to those skilled in the art and need not be described further herein.

According to embodiments of the present invention, the cup 430 may be formed from material that shields the photodetector 432 from external light, as well as from direct light from the light source (i.e., light from the light source 420 that does not pass through the egg). An exemplary material includes, but is not limited to, silicone with a dark (e.g., black, etc.) colorant. The cup 430 may have any of various shapes and sizes and is not limited to the illustrated configuration.

In operation, processor (e.g., 650, FIG. 8) communicates with the photodetector 432 in each detector tool 412. The processor 650 is configured to process an output signal generated by each photodetector 432 and to identify cyclical and non-cyclical intensity variations of light passing through each egg 1. Cyclical variations in light intensity can indicate the existence of an embryo pulse, while non-cyclical variations in light intensity can indicate embryo movement.

In addition to sensing variations in light level, the photodetector 432 provides an average light level in an egg that can be used to provide other important information about egg condition. For example, the average light reflected to the photodetector 432 from a clear egg will be greater than the average light reflected from a live Day 18 egg because the broad beam of light from the light source that impinges upon the side of the egg will reflect throughout the egg rather than being absorbed by a large embryo. Similarly, the average light reaching the photodetector 432 from an upside down egg will be less than that from a normally positioned egg (blunt end up) because more of the embryo is available to block the light. These effects may be enhanced by using a light source having a different wavelength than the a light source that is optimal for detecting heartbeat. If multiple light sources with multiple wavelengths are used then their outputs may be time multiplexed to allow sensing of each wavelength or light source separately with the single photodetector 432.

Embodiments of the present invention are not limited to the configuration of the illustrated detector tool 412, including cup 430 and light source 420. The cup 430 may have various shapes, sizes and configurations. Moreover, the light source 420 may have various shapes, sizes and configurations. For example, multiple light sources may be associated with each detector tool 412.

Figure 7A:
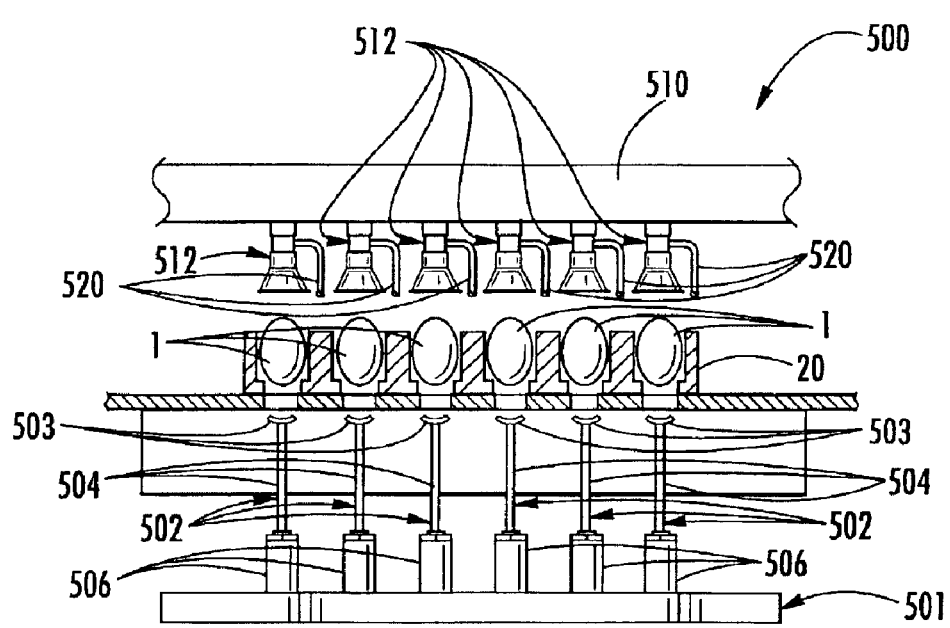
FIG. 7A is a side elevation view of an apparatus for identifying live eggs according to embodiments of the present invention, wherein the egg support is in the retracted position.
Figure 7B:
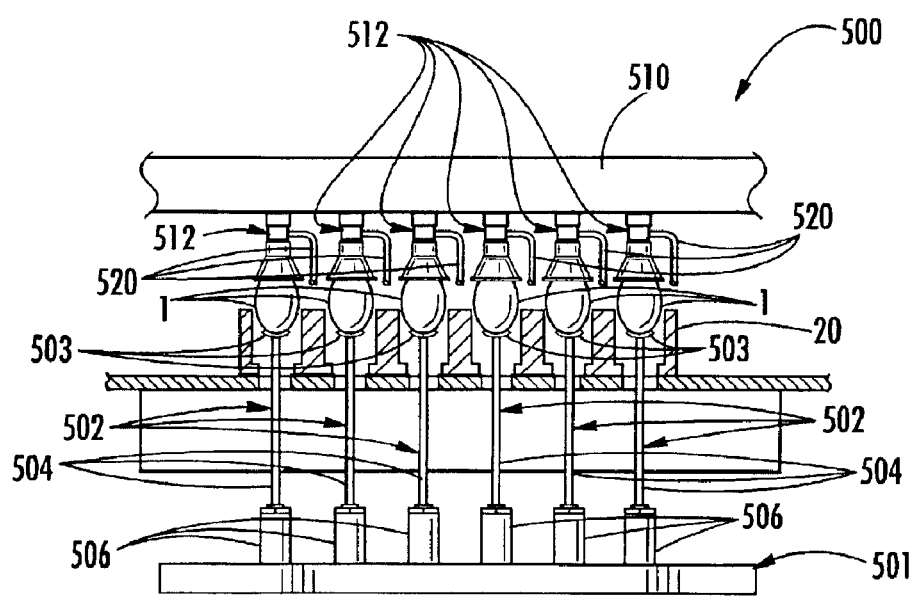
FIG. 7B illustrates the apparatus of FIG. 7A with the egg support is in the extended position.
Figure 7C:
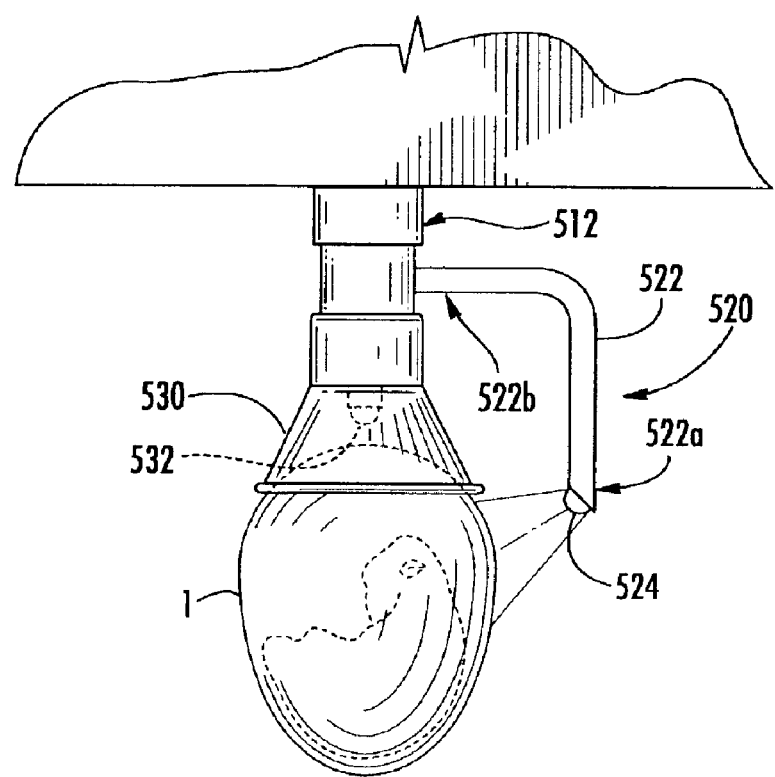
FIG. 7C is an enlarged view of one of the detector tools of FIGS. 7A–7B.

Referring to FIGS. 7A–7C, an apparatus 500 for identifying live eggs according to other embodiments of the present invention is illustrated. The apparatus 500 includes a plurality of egg support apparatus 502, each configured to raise an egg from an egg flat (or other carrier) into contact with an overhead detector tool 512. Each illustrated egg support 502 is secured to a frame 501 and includes a respective cradle 503 that is configured to retain an egg 1 therein. In the illustrated embodiment, each cradle 503 is secured to an elongated member 504 that is extended and retracted via a respective actuator device 506. Each egg support 502 is independently movable between a retracted position (FIG. 7A) and an extended position (FIG. 7B). The actuator devices 506 may be virtually any type of device capable of raising and lowering a respective plurality of egg supports 502. Exemplary actuators include, but are not limited to, mechanical (e.g., spring) actuators, solenoid actuators, pneumatic actuators, and hydraulic actuators. Each egg support 502 is configured to support an egg 1 via a cradle 503 and to move the egg 1 upwardly from the egg flat 20 with a predetermined force such that the egg becomes seated with a respective detector tool cup 530. Because egg heights can vary, the independent raising of each egg support 502 allows each egg 1 to be seated properly with a detector tool cup 530.

Embodiments of the present invention are not limited to the illustrated egg support apparatus 502. An egg support apparatus that raises an egg from an egg flat upwardly into contact with a detector tool cup 530, according to embodiments of the present invention, may have various shapes, sizes and configurations.

A frame 510 is positioned above an egg flat 20 in overlying relationship, as illustrated. A plurality of detector tools 512 depend from the frame 510 in generally vertical orientations, as illustrated. A light source 520 depends from each detector tool 512, as illustrated. Each light source 520 is configured to be positioned adjacent a portion of an egg 1 when an egg support apparatus 502 is in the extended position (FIG. 7B). Each light source 520 is configured to illuminate an egg 1 with light from one or more selected portions of the spectrum. For example, each light source 520 may be configured to illuminate an egg with light in the visible portion of the spectrum and/or light from the infrared portion of the spectrum.

In the illustrated embodiment, the light source 520 includes an elongated stalk 522 having a free end 522a. An opposite end 522b is secured to the detector tool 512. A light-emitting element (e.g., one or more light emitting diodes) 524 is positioned at the stalk free end 522a. According to embodiments of the present invention, a plurality of light-emitting elements may be positioned at the stalk free end 522a.

A cup 530 is attached to the detector tool 512, as illustrated, and is configured to overlie a portion of an egg 1 in contacting relationship therewith when the egg support apparatus 502 is in the extended position. A photodetector 532 is disposed within each cup 530 and is configured to generate an output signal corresponding to the intensity of light leaving an egg 1. As described above with respect to FIGS. 6A–6C, the cup 530 may be formed from material that shields the photodetector 532 from external light, as well as from direct light from the light source (i.e., light from the light source 520 that does not pass through the egg). An exemplary material includes, but is not limited to, silicone with a dark (e.g., black, etc.) colorant. As described above with respect to FIGS. 6A–6C, various amplifiers and filters may be utilized to block unwanted noise and other wavelengths of light.

In operation, processor (e.g., 650, FIG. 8) communicates with the photodetector 532 in each detector tool 512. The processor 650 is configured to process an output signal generated by the photodetector 532 and to identify cyclical and non-cyclical intensity variations of light passing through each egg 1.

Embodiments of the present invention are not limited to the configuration of the illustrated photodetector tool 512, including cup 530 and light source 520. The cup 530 may have various shapes, sizes and configurations. Moreover, the light source 520 may have various shapes, sizes and configurations. In addition, each elongated stalk 522 may depend from the frame 510.

Figure 8:
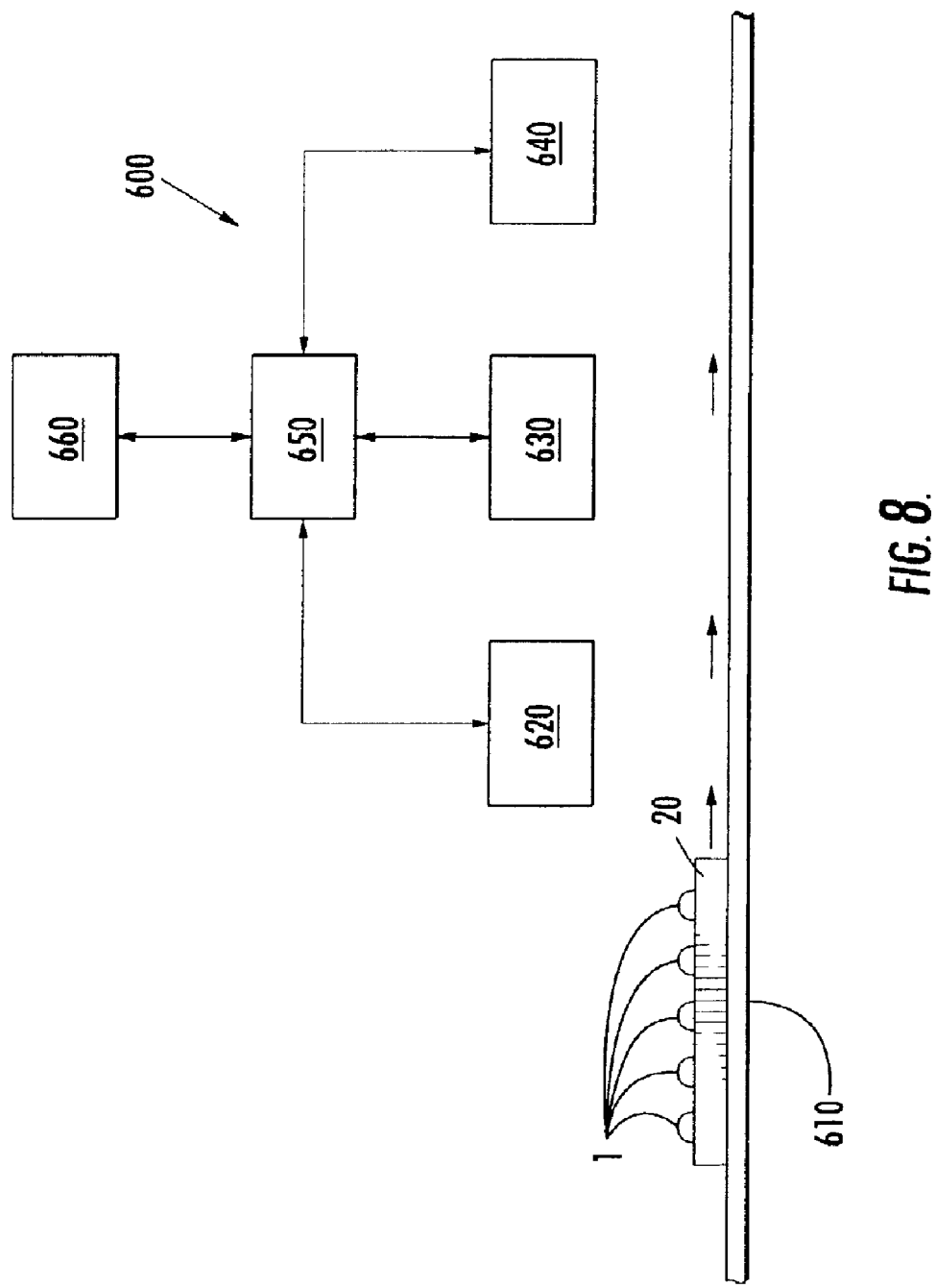
FIG. 8 is a block diagram of an egg processing system, according to embodiments of the present invention.

Referring to FIG. 8, a block diagram of an egg processing system 600, according to embodiments of the present invention, is illustrated. The illustrated egg processing system 600 includes a conveyor system 610 that conveys flats (or other containers) 20 of eggs 1, an identifier station 620 operably associated with the conveyor system 610 that identifies live eggs, an egg removal station 630 that is configured to selectively remove eggs (e.g., live or non-live eggs) from an egg flat 20, and an egg processing station 640.

In operation, a flat 20 of eggs 1 is conveyed via the conveyor system 610 to the identifier station 620 that is configured to designate each egg 1 within the flat 20 as being either live or non-live based upon detection of embryo pulse and/or embryo motion as discussed above with respect to FIGS. 6A–6C and 7A–7B. Various types of conveyor systems may be utilized with embodiments of the present invention. Egg conveying systems are well known to those of skill in the art and need not be described further herein.

Although eggs conventionally are carried in egg flats, any type of container for carrying eggs to the identifier station 620, as well as to the other egg processing equipment. Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

According to embodiments of the present invention, the identifier station 620 may include the embodiments of FIGS. 6A–6C or the embodiments of FIGS. 7A–7B. The controller 650 controls operations of the identifier station 620 and stores information about each egg 1 (e.g., whether each egg is live, non-live, or uncertain). An operator interface (e.g., a display) 660 may be provided to allow an operator to interact with the controller 650. The controller 650 may control other egg processing operations, as well, including the conveyor system 610, the egg removal station 630, and the egg processing station 640.

Eggs designated as non-live may be removed from the flat 20 via egg removal station 630. The egg removal station 630 may be a manual station wherein the designated non-live eggs are removed by hand. Alternatively, the egg removal station 630 may operate automatically and robotically. For example, the egg removal station 630 may employ suction-type lifting devices as disclosed in U.S. Pat. No. 4,681,063 or in U.S. Pat. No. 5,017,003, the disclosures of which are hereby incorporated by reference in their entireties. Various devices and methods for automatically and robotically removing eggs from a flat and transporting same to another location may be utilized with embodiments of the present invention without limitation. Exemplary egg removal apparatus that may serve the function of the egg removal station 630 are described in U.S. Pat. Nos. 6,145,668; 6,149,375; 6,213,709; and 6,224,316, each of which is incorporated herein by reference in its entirety.

Eggs identified as non-live are removed from the flat 20 at the egg removal station 630 and are discarded or may be subjected to other processing. Flat 20 at this point on the conveyor 610 contains only live eggs and can proceed to processing station 640 (e.g., inoculation, vaccine production, etc.). An exemplary device for in ovo injection of substances into a plurality of eggs in accordance with embodiments of the present invention is the INOVOJECT® automated injection system (Embrex, Inc., Research Triangle Park, North Carolina). However, any in ovo injection device may be suitable for use according to embodiments of the present invention. Suitable injection devices preferably are designed to operate in conjunction with commercial egg carrier devices or flats.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of identifying live eggs, comprising:
   contacting an egg with a cup such that the cup overlies a portion of the egg in contacting relationship therewith;
   illuminating the egg with light from one or more selected portions of the spectrum via a light source positioned adjacent the egg;
   detecting intensity of light leaving the egg via a photodetector positioned within the cup;
   generating an output signal that corresponds to detected light intensity;
   processing the output signal to identify cyclical and non-cyclical variations in light intensity, wherein cyclical variations in light intensity indicate the existence of an embryo pulse, and wherein non-cyclical variations in light intensity indicate embryo movement; and
   designating the egg as a live egg in response to identifying cyclical or non-cyclical variations in light intensity.

2. The method of claim 1, wherein illuminating the egg with light comprises illuminating the egg with light from the infrared portion of the spectrum.

3. The method of claim 1, wherein illuminating the egg with light comprises illuminating the egg with light from the visible and infrared portions of the spectrum.

4. A method of processing eggs, comprising:
   illuminating each of a plurality of eggs with light from a light source;
   detecting light leaving each egg via a respective photodetector positioned adjacent each egg, wherein each photodetector generates a respective output signal that corresponds to intensity of light leaving a respective egg;
   processing each output signal to identify cyclical variations in light intensity, wherein a cyclical variation in light intensity indicates the existence of an embryo pulse;
   designating each egg indicated to have an embryo pulse as a live egg; and
   selectively processing eggs designated as live eggs, comprising:
      extracting material from each egg designated as being live;
      assaying the material extracted from each egg to identify live eggs having one or more characteristics; and
      selectively processing live eggs identified as having the one or more characteristics.

5. The method of claim 4, further comprising processing each output signal to identify non-cyclical variations in light intensity, wherein non-cyclical variations in light intensity indicate embryo movement.

6. The method of claim 4, wherein illuminating each egg with light comprises illuminating each egg with light from the infrared portion of the spectrum.

7. The method of claim 4, wherein illuminating each egg with light comprises illuminating each egg with light from the visible and/or infrared portions of the spectrum.

8. The method of claim 4, wherein extracting material from each egg comprises extracting allantoic fluid, amnion, yolk, shell, albumen, tissue, membrane and/or blood from each egg.

9. The method of claim 4, wherein assaying the material extracted from each egg to identify live eggs having one or more characteristics comprises identifying the gender of each egg.

10. The method of claim 9, wherein selectively processing live eggs identified as having the one or more characteristics comprises injecting a substance into the eggs according to gender.

11. The method of claim 10, wherein the substance comprises a vaccine.

12. The method of claim 10, wherein the substance comprises a virus.

13. The method of claim 4, wherein assaying the material extracted from each egg to identify live eggs having one or more characteristics comprises identifying the gender of each egg, and wherein selectively processing live eggs identified as having the one or more characteristics comprises removing eggs identified as having the same gender.

14. The method of claim 4, wherein selectively processing eggs designated as live eggs comprises injecting a substance into the live eggs.

15. The method of claim 4, wherein selectively processing eggs designated as live eggs comprises removing material from the live eggs.

16. The method of claim 4, further comprising removing eggs not designated as live eggs.

17. An apparatus for identifying live eggs, comprising:
   a generally horizontal frame movable between raised and lowered positions;
   a detector tool supported by the frame in a generally vertical orientation and movable with the frame between the raised and lowered positions, comprising:
      a light source configured to be positioned adjacent a first portion of an egg when the frame is in the lowered position and wherein the light source is configured to illuminate the egg with light from one or more selected portions of the spectrum;
      a cup configured to overlie a second portion of the egg in contacting relationship therewith when the frame is in the lowered position; and
      a photodetector disposed within the cup that generates an output signal corresponding to intensity of light leaving the egg; and
   a processor in communication with the photodetector that processes the output signal to identify cyclical variations in light intensity, wherein a cyclical variation in light intensity indicates the existence of an embryo pulse.

18. The apparatus of claim 17, wherein the processor also processes the output signal to identify non-cyclical variations in light intensity, wherein non-cyclical variations in light intensity indicate embryo movement.

19. The apparatus of claim 17, wherein the light source illuminates the egg with light from the infrared portion of the spectrum.

20. The apparatus of claim 17, wherein the light source illuminates the egg with light from the visible and/or infrared portions of the spectrum.

21. The apparatus of claim 17, wherein the cup comprises material configured to shield the photodetector from external light and from direct light from the light source.

22. The apparatus of claim 17, wherein a vacuum can be produced within the cup to facilitate scaling the cup with the egg.

23. The apparatus of claim 17, wherein the light source comprises an elongated stalk having a free end, and wherein one or more light-emitting elements are positioned adjacent the stalk free end.

24. An apparatus for identifying live eggs, comprising:
an egg support configured to support an egg in a predetermined position, wherein the egg support is movable between retracted and extended positions;
a frame overlying the egg support;
a detector tool supported by the frame in a generally vertical orientation, comprising:
a light source configured to be positioned adjacent a first portion of an egg when the egg support is in the extended position and wherein the light source is configured to illuminate the egg with light from one or more selected portions of the spectrum;
a cup configured to overlie a second portion of the egg in contacting relationship therewith when the egg support is in the extended position; and
a photodetector disposed within the cup that generates an output signal corresponding to intensity of light leaving the egg; and
a processor in communication with the photodetector that processes the output signal to identify cyclical variations in light intensity, wherein a cyclical variation in light intensity indicates the existence of an embryo pulse.

25. The apparatus of claim 24, wherein the processor also processes the output signal to identify non-cyclical variations in light intensity, wherein non-cyclical variations in light intensity indicate embryo movement.

26. The apparatus of claim 24, wherein the light source illuminates the egg with light from the infrared portion of the spectrum.

27. The apparatus of claim 24, wherein the light source illuminates the egg with light from the visible and/or infrared portions of the spectrum.

28. The apparatus of claim 24, wherein the cup comprises material configured to shield the photodetector from external light and from direct light from the light source.

29. The apparatus of claim 24, wherein a vacuum can be produced within the cup to facilitate sealing the cup with the egg.

30. The apparatus of claim 24, wherein the light source comprises an elongated stalk having a free end, and wherein one or more light-emitting elements are positioned adjacent the stalk free end.

31. An egg processing system, comprising:
a conveyor that conveys flats of eggs;
an identifier operably associated with the conveyor that identifies live eggs, comprising:
a frame movable between raised and lowered positions;
a plurality of detector tools supported by the frame in generally vertical orientations and movable with the frame between the raised and lowered positions, each detector tool comprising:
a light source configured to be positioned adjacent a first portion of an egg when the frame is in the lowered position and wherein the light source is configured to illuminate the egg with light from one or more selected portions of the spectrum;
a cup configured to overlie a second portion of the egg in contacting relationship therewith when the flame is in the lowered position; and
a photodetector disposed within the cup that generates an output signal corresponding to intensity of light leaving the egg; and
a processor in communication with the photodetectors that processes the output signal from each photodetector to identify cyclical variations in light intensity, wherein a cyclical variation in light intensity indicates the existence of an embryo pulse.

32. The egg processing system of claim 31, further comprising an egg removal apparatus configured to remove non-live eggs from the egg flat.

33. The egg processing system of claim 31, further comprising a plurality of sample heads operably associated with the conveyor, each of which is configured to extract material from a respective egg in an egg flat and to deposit the extracted material within a respective sample receptacle.

34. The egg processing system of claim 31, further comprising a plurality of injectors, wherein each injector is configured to inject a substance into a respective egg identified as a live egg.

35. The egg processing system of claim 31, further comprising a plurality of injectors, wherein each injector is configured to remove material from a respective egg identified as a live egg.

36. The egg processing system of claim 31, wherein the processor also processes the output signal to identify non-cyclical variations in light intensity, wherein non-cyclical variations in light intensity indicate embryo movement.

37. The egg processing system of claim 31, wherein each light source illuminates the egg with light from the infrared portion of the spectrum.

38. The egg processing system of claim 31, wherein each light source illuminates the egg with light from the visible and/or infrared portions of the spectrum.

39. The egg processing system of claim 31, wherein each cup comprises material configured to shield the photodetector from external light and from direct light from the light source.

40. The egg processing system of claim 31, wherein a vacuum can be produced within the cup to facilitate sealing the cup with the egg.

41. The egg processing system of claim 31, wherein each light source comprises an elongated stalk having a free end, and wherein one or more light-emitting elements are positioned adjacent the stalk free end.

42. A method of processing eggs, comprising:
illuminating each of a plurality of eggs with light from a light source;
detecting light leaving each egg via a respective photodetector positioned adjacent each egg, wherein each photodetector generates a respective output signal that corresponds to intensity of light leaving a respective egg;
processing each output signal to identify cyclical variations in light intensity, wherein a cyclical variation in light intensity indicates the existence of an embryo pulse;
designating each egg indicated to have an embryo pulse as a live egg; and
injecting a substance into eggs designated as live eggs.

43. The method of claim 42, further comprising processing each output signal to identity non-cyclical variations in light intensity, wherein non-cyclical variations in light intensity indicate embryo movement.

44. The method of claim 42, wherein illuminating each egg with light comprises illuminating each egg with light from the infrared portion of the spectrum.

45. The method of claim 42, wherein illuminating each egg with light comprises illuminating each egg with light from the visible and/or infrared portions of the spectrum.

46. The method of claim 42, wherein the substance comprises a vaccine.

47. The method of claim 42, wherein the substance comprises a virus.

48. A method of processing eggs, comprising:
    illuminating each of a plurality of eggs with light from a light source;
    detecting light leaving each egg via a respective photodetector positioned adjacent each egg, wherein each photodetector generates a respective output signal that corresponds to intensity of light leaving a respective egg;
    processing each output signal to identify cyclical variations in light intensity, wherein a cyclical variation in light intensity indicates the existence of an embryo pulse;
    designating each egg indicated to have an embryo pulse as a live egg; and
    removing material from eggs designated am live eggs.

49. The method of claim 48, further comprising processing each output signal to identify non-cyclical variations in light intensity, wherein non-cyclical variations in light intensity indicate embryo movement.

50. The method of claim 48, wherein illuminating each egg with light comprises illuminating each egg with light from the infrared portion of the spectrum.

51. The method of claim 48, wherein illuminating each egg with light comprises illuminating each egg with light from the visible and/or infrared portions of the spectrum.

52. The method of claim 48, wherein removing material comprises removing allantoic fluid, amnion, yolk, shell, albumen, tissue, membrane and/or blood.

53. A method of processing eggs, comprising:
    illuminating each of a plurality of eggs with light from a light source;
    detecting light leaving each egg via a respective photodetector positioned adjacent each egg, wherein each photodetector generates a respective output signal that corresponds to intensify of light leaving a respective egg;
    processing each output signal to identify cyclical variations in light intensity, wherein a cyclical variation in light intensity indicates the existence of an embryo pulse;
    designating each egg indicated to have an embryo pulse as a live egg;
    selectively processing eggs designated as live eggs; and
    removing eggs not designated as live eggs.

54. The method of claim 53, further comprising processing each output signal to identify non-cyclical variations in light intensity, wherein non-cyclical variations in light intensity indicate embryo movement.

55. The method of claim 53, wherein illuminating each egg with light comprises illuminating each egg with light from the infrared portion of the spectrum.

56. The method of claim 53, wherein illuminating each egg with light comprises illuminating each egg with light from the visible and/or infrared portions of the spectrum.

57. The method of claim 53, wherein selectively processing eggs designated as live eggs comprises injecting a substance into the live eggs.

58. The method of claim 53, wherein selectively processing eggs designated as live eggs comprises removing material from the live eggs.

* * * * *

UNITED STATES PATENT AND TRADEMARK OFFICE
CERTIFICATE OF CORRECTION

PATENT NO. : 6,860,225 B2
DATED : March 1, 2005
INVENTOR(S) : Hebrank

It is certified that error appears in the above-identified patent and that said Letters Patent is hereby corrected as shown below:

Column 12,
Line 66, should read -- produced within the cup to facilitate sealing the cup with the --

Signed and Sealed this

Fourteenth Day of June, 2005

JON W. DUDAS
*Director of the United States Patent and Trademark Office*